United States Patent
Paio et al.

(10) Patent No.: US 9,970,042 B2
(45) Date of Patent: May 15, 2018

(54) ENZYMATIC PROCESS FOR THE PREPARATION OF TESTOSTERONE AND ESTERS THEREOF

(71) Applicant: F.I.S.- FABBRICA ITALIANA SINTETICI S.P.A., Montecchio Maggiore (VI) (IT)

(72) Inventors: Alfredo Paio, Montecchio Maggiore (VI) (IT); Stefano Fogal, Montecchio Maggiore (VI) (IT); Riccardo Motterle, Montecchio Maggiore (VI) (IT)

(73) Assignee: F.I.S.-FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 122 days.

(21) Appl. No.: 15/206,582

(22) Filed: Jul. 11, 2016

(65) Prior Publication Data

US 2017/0029863 A1   Feb. 2, 2017

(30) Foreign Application Priority Data

Jul. 29, 2015 (EP) .................................. 15178820

(51) Int. Cl.
| | |
|---|---|
| *C12P 33/00* | (2006.01) |
| *C12P 33/18* | (2006.01) |
| *C12N 9/20* | (2006.01) |
| *C07J 9/00* | (2006.01) |

(52) U.S. Cl.
CPC ............... *C12P 33/005* (2013.01); *C07J 9/00* (2013.01); *C12N 9/20* (2013.01); *C12P 33/18* (2013.01); *C12Y 301/01003* (2013.01)

(58) Field of Classification Search
CPC .......... C12P 33/005; C12P 33/18; C12N 9/20; C07J 9/00; C12Y 301/01003
See application file for complete search history.

(56) References Cited

U.S. PATENT DOCUMENTS 5,827,719 A   10/1998   Sandal et al.

FOREIGN PATENT DOCUMENTS

| WO | 9735956 A1 | 10/1997 |
| WO | 0034450 A1 | 6/2000 |
| WO | 0192502 A1 | 12/2001 |
| WO | 2015085920 A1 | 6/2015 |

OTHER PUBLICATIONS

Labaree D. et al., "A direct stereoselective synthesis of 7-beta-hydrocytestosterone", Steroid, Jun. 1997, vol. 62, No. 6, pp. 482-486. (Year: 1997).*

Njar V. C.O. et al., "Enzymatic transesterification of steroid esters in organic solvents", Tetrahedron Letters, 1987, vol. 28, Issue 52, pp. 6549-6552. (Year: 1987).*

* cited by examiner

*Primary Examiner* — Satyendra K Singh
(74) *Attorney, Agent, or Firm* — Lucas & Mercanti, LLP

(57) ABSTRACT

The present invention relates to a new process for the preparation of testosterone by means of enzymatic hydrolysis of testosterone esters.

12 Claims, No Drawings

ENZYMATIC PROCESS FOR THE PREPARATION OF TESTOSTERONE AND ESTERS THEREOF

CROSS-REFERENCE TO RELATED APPLICATIONS

This application claims the benefit of priority from European Patent Application No. 15178820, filed Jul. 29, 2015, the contents of which are incorporated herein by reference.

TECHNICAL FIELD

The present invention relates to a process for the preparation of testosterone by means of enzymatic hydrolysis of testosterone esters thereof.

BACKGROUND ART

Testosterone of formula (I):

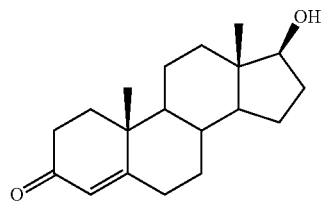

also named (17β)-17-hydroxyandrost-4-en-3-one, is a steroid, a known human hormone and an active ingredient largely employed for pharmaceutical purposes.

It is well known that for hydrolyzing esters compounds, basic medium can be successful employed, in particular, aqueous soda is a typical reagent. Therefore, it is well known to the skilled person aimed to prepare testosterone that aqueous caustic soda can be used to convert by hydrolysis testosterone esters into testosterone.

Nevertheless, experimental attempts to convert testosterone esters to testosterone by using aqueous caustic soda provides testosterone having a large amounts of several unknown impurities, which are very difficult to be eliminated from the product, for example through re-crystallization procedures.

Several other methods for the preparation of testosterone have been disclosed. In particular, some of them describe the transformation of said steroid by means of enzymatic hydrolysis.

Specifically, Tetrahedron Letters, 28 (52), 6549-6552, 1987 discloses a procedure for the conversion of steroid esters into the corresponding alcohols, i.e. steroids, via enzymatic transesterification in organic solvent. Said enzymatic transformation, after an initial screening of a number of hydrolytic enzymes, revealed that lipase from *Candida cylyndracea* was found to be the best catalyst to hydrolyse steroid esters with octanol in organic solvents. The results of some reactions are shown in the table of said article at pages 6551-6552, in particular testosterone esters substrates were tested with said lipase catalyst (see entry 9 and 10). The results show how the lipase from *Candida cylyndracea* did not produce any conversion of testosterone acetate to testosterone, as well as the same reaction with testosterone propionate gives 12% of conversion, only. Furthermore, this enzymatic reaction was carried out in organic solvents with a high amount of enzyme and a low amount of substrate.

The publication Steroids, 62, 482-486, 1997 discloses a direct stereoselective synthesis of a testosterone derivative, being the 7β-hydroxytestosterone (9) by enzymatic oxidation followed by an enzymatic hydrolysis. In particular, said method describes the use of porcine lipase to obtain the compound (9), from the intermediate ester. This enzymatic hydrolysis using said lipase, from porcine pancreas, produces a conversion of 7β,17β-dihydroxy-4-androsten-3-one 17-caprylate (8) to 7β-hydroxytestosterone (9). The H-NMR spectrum of the compound (9) shows the absence of the ester group. At the same time, said conversion results in a 75% yield but the product needed to be purified by flash column chromatography. Therefore said method is not suitable for large productions. Moreover, it is observed that the product obtained by such enzymatic hydrolysis, is the compound (9), which is 7β-hydroxytestosterone, i.e. a different compound than testosterone.

Finally, Acta Chemica Scandinavica 27, 1240-1248, 1973 discloses a transformation of steroids by cell-free preparation of *Penicillium lilacinum* NRRL 895; the latter shows to contain inducible steroid esterase activity. The article describes the steroid transforming capacity of the fungus *Penicillium lilacinum* that was tested on several steroidal compounds, in particular, on testosterone and esters thereof.

In the specific case, in two experiments testosterone acetate was readily hydrolysed to testosterone with conversions of 80.3% and 83.8% (see pag. 1246). Nevertheless, the use of such esterase from said cell-free on other testosterone esters like testosterone propionate provides only partial hydrolysis, whereas testosterone enanthate, benzoate and hemisuccinate were unaffected. Moreover, it should be taken in account that these results were obtained, and in particular the transformation of testosterone acetate to testosterone, at very low concentration of the substrate, were unsuitable for commercial and/or industrial productions.

SUMMARY OF INVENTION

The problem addressed by the present invention is therefore that of providing an improved process for the preparation of testosterone, in particular which allows a high conversion of testosterone esters to testosterone and/or provides testosterone with high chemical purity.

This problem is solved by a process for the preparation of testosterone as outlined in the annexed claims, whose definitions are integral part of the present description.

Particularly, the present invention provides a process for producing the active ingredient testosterone by means of enzymatic hydrolysis of testosterone ester of formula (II):

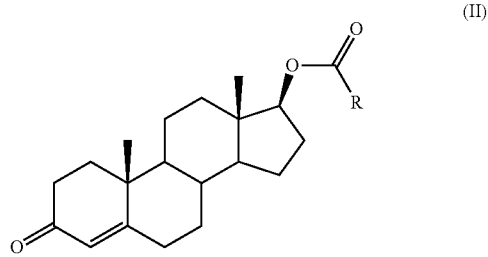

wherein R is a $C_1$-$C_9$ linear or branched alkyl group or is $C_3$-$C_9$ cyclic or branched cyclic alkyl group.

Preferably, said enzymatic hydrolysis is carried out by the lipase Novozym® 51032 that is a lipase from *Aspergillus oryzae* or by the lipase from *Candida antarctica* A.

In a further aspect, the present invention provides the use of a lipase in pure form for the enzymatic hydrolysis of compound of formula (II), in particular, wherein the lipase is from *Aspergillus oryzae* or lipase from *Candida antarctica* A.

Another object of the invention is a process for the preparation of a testosterone ester of formula (III):

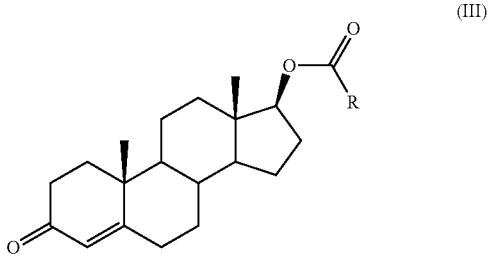

(III)

wherein R is a $C_1$-$C_9$ linear or branched alkyl group or is $C_3$-$C_9$ cyclic or branched cyclic alkyl group, which is based on the same inventive concept of the enzymatic hydrolysis carried out with the enzymes of the invention.

DETAILED DESCRIPTION

One of the several known synthetic routes to produce testosterone consists of hydrolyzing testosterone ester, in particular, under basic conditions.

However, this kind of reaction produces many impurities which are difficult to be eliminate, for example, by re-crystallization. Some of these remain in high quantity, especially in amounts higher than 0.10%, which is not acceptable for a pharmaceutical active substance such as testosterone.

Considering said results, a different and improved synthesis was considered in order to produce testosterone starting from testosterone esters and to produce testosterone having a high degree of chemical purity.

Object of the present invention is thus an improved process for the preparation of testosterone of formula (I):

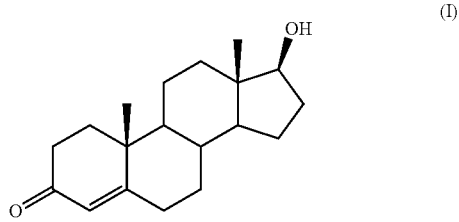 [SMILES: C[C@]12CCC(=O)C=C1CCC1C2CC[C@@]2(C)C1CC[C@@H]2O]

(I)

by enzymatic hydrolysis of a testosterone ester of formula (II):

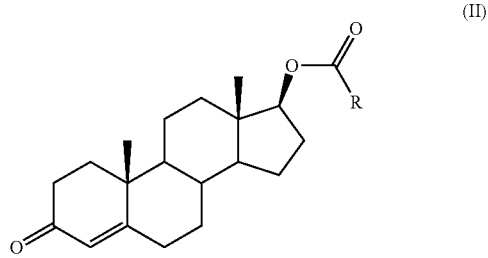

(II)

wherein R is a $C_1$-$C_9$ linear or branched alkyl group or is a $C_3$-$C_9$ cyclic or branched cyclic alkyl group, characterized in that the enzyme is a lipase from *Aspergillus oryzae* or is a lipase from *Candida antarctica* A.

It has been indeed surprisingly found that specific kind of enzymes, being lipase from *Aspergillus oryzae* or lipase from *Candida antarctica* A, produce a complete hydrolysis of said esters, and, at the same time, provide testosterone having very high chemical purity since the reaction is extremely regioselective, the optical configuration of the asymmetric carbon in 17-position is completely retained and, remarkably, no other impurities are formed during said process. Since no other impurities are formed during the conversion of testosterone esters of formula (II) to testosterone, the chemical purity of testosterone reflects the chemical purity of the starting testosterone esters. Thus, if the starting testosterone esters have high chemical purity, the process of the present invention provides testosterone having high chemical purity as well. In other words, the process is extremely regioselective and efficient so that testosterone esters are converted only to testosterone, not to other impurity compounds.

The process of the present invention of enzymatic hydrolysis of a testosterone ester of formula (II) is typically carried out in a buffered aqueous medium. Particularly, it is carried out in a buffered aqueous wherein the buffer is phosphate buffer. More particularly, the buffered aqueous medium is made by a phosphate buffer and has a pH comprised between 6 and 11.

In the compound of formula (II) R is a $C_1$-$C_9$ linear or branched alkyl group or is $C_3$-$C_9$ cyclic or branched cyclic alkyl group.

In the compound of formula (II) R is a $C_1$-$C_9$ linear or branched alkyl group selected from the group of methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 3-ethylbutyl, 1,1-diethylethyl, 1-propylpropyl, etc.

In the compound of formula (II) R can also be a $C_3$-$C_9$ cyclic or branched cyclic alkyl group selected from the group of cyclopropyl, cyclobutyl, cyclopentyl, cyclohexyl, cycloheptyl, cyclooctyl, cyclononyl, cycloproprylmethyl, cyclopropylethyl, cyclopropylpropyl, 3-cyclopentylethyl, etc.

The enzyme is a lipase from *Aspergillus oryzae*, i.e. is a lipase originating from an *Aspergillus oryzae* micro-organism. Said enzyme is commercially available, for example from Sigma-Aldrich Inc. (USA) with product code 62285.

The enzyme, lipase from *Aspergillus oryzae*, can also be a lipase originated from a genetically modified *Aspergillus oryzae* micro-organism.

Preferably, said enzyme is an engineered protein which is produced by submerged fermentation of a genetically modified *Aspergillus oryzae* micro-organism followed by separation and purification from the production organism.

According to a preferred embodiment of the invention, the lipase from *Aspergillus oryzae* is the lipase Novozym® 51032, an enzyme provided by Novozymes A/S (Denmark), the product data sheet therefor is hereby incorporated herein by reference.

Said Novozym® 51032 is used for the hydrolysis of triglycerides and polyvinyl acetate.

The enzyme of the process of the invention can also be a lipase from *Humicola insolens*, said lipase could also be produced from a different organism, for example from *Aspergillus oryzae*.

The enzyme of the process of the invention is a lipase from *Humicola insolens*, wherein the DNA sequence encoding the *Humicola insolens* lipase is genetically modified or not genetically modified.

The DNA sequence encoding the *Humicola insolens* lipase means that there is a specific DNA sequence inside the micro-organism *Humicola insolens*, said sequence, made up of nitrogen bases, encodes an amino acid sequence of a protein, as known by the skilled person. Specifically, in the present invention, the DNA sequence of *Humicola insolens* contains the information, specifically the nitrogen bases inside of DNA of *Humicola insolens*, and this information encodes the amino acid sequence of the enzyme, i.e. of the *Humicola insolens* lipase.

The DNA sequence encoding the *Humicola insolens* lipase is genetically modified or not genetically modified, which means that in the first case *Humicola insolens* lipase comprises a substitution of one or more amino acid residues. In particular a number of variants of *Humicola insolens* lipase have been disclosed. See, for example, U.S. Pat. No. 5,827,719, WO 00/34450, WO 01/92502, and WO 2015/085920, the contents of each of which are incorporated herein by reference.

Not genetically modified means that *Humicola insolens* lipase comprises the non-substitution of amino acid residues, therefore the specific DNA sequence encoding the *Humicola insolens* lipase is wild type. In particular the amino acid sequence of a lipase from *Humicola insolens* has been published in U.S. Pat. No. 5,827,719, the contents of which are incorporated herein by reference.

According to a preferred embodiment of the invention, *Humicola insolens* lipase is produced by the host cell, wherein the host cell is *Aspergillus oryzae*. Preferably, the production organism of said lipase is *Aspergillus oryzae* and the donor organism is *Humicola insolens*, more preferably the recombinant form of *Humicola insolens* lipase is produced by *Aspergillus oryzae*.

The recombinant production means that the production organism, called host, produces an enzyme or another protein based on the DNA sequence, encoding said enzyme or said other protein, belonging to another donor organism.

Host cell means any cell type that is susceptible to transformation, transfection, transduction or comprising a DNA construct or an expression vector which carries the DNA sequence encoding the enzyme of the present invention, *Humicola insolens* lipase.

The host cell can be a bacterial cell, a fungal cell or another micro-organism cell.

Examples of bacteria are gram positive bacteria such as *Bacillus lentus, Bacillus coagulans, Bacillus lautus*; or gram negative bacteria such *E. coli*.

Examples of filamentous fungus are *Aspergillus oryzae, Aspergillus niger* or *Fusarium oxysporum*, and the method for producing the host cell, specifically the host fungus, is disclosed in WO 97/35956, the contents of which are incorporated herein by reference.

Preferably, in the process of the present invention, the host cell is *Aspergillus oryzae*.

According to a preferred embodiment of the invention, the lipase from *Humicola insolens*, wherein the DNA sequence encoding the *Humicola insolens* lipase is genetically modified, is the Novozym® 51032.

According to a more preferred embodiment of the invention, the lipase from *Humicola insolens*, wherein the DNA sequence encoding the *Humicola insolens* lipase is genetically modified and it is produced by *Aspergillus oryzae*, is the Novozym® 51032.

Novozym® 51032 is a lipase with lower activity of 15 KLU/g. Said enzyme is yellow to light brown color and is in liquid form.

According to a preferred embodiment of the invention, the lipase from *Humicola insolens* is a cutinase.

Cutinase means a specific kind of lipase enzyme, or better is a lipolytic enzyme having cutinase activity, i.e. capable of hydroliyzing the substrate cutin, or better that catalyzes the following reaction: Cutin+$H_2O$⇌Cutin monomers. The cutinase of the present invention is the enzyme capable of hydroliyzing Testosterone esters of formula (II) to Testosterone (I).

The preferred cutinase of the present invention is encoded from *Humicola insolens*, wherein the DNA sequence encoding the *Humicola insolens* lipase, or better is a *Humicola insolens* cutinase, which is genetically modified or not genetically modified. Moreover said *Humicola insolens* cutinase is preferably produced by *Aspergillus oryzae*.

Therefore Novozym® 51032 is a cutinase from *Humicola insolens*, i.e. a specific kind of lipase enzyme, wherein the DNA sequence encoding said *Humicola insolens* cutinase is genetically modified. In particular said Novozym® 51032 is produced in the host cell, being *Aspergillus oryzae*, i.e. the latest fungus comprises the DNA construct or the expression vector that encodes the enzyme of the present invention, i.e. *Humicola insolens* cutinase. Finally said enzyme is separated and purified from the production organism, i.e. *Aspergillus oryzae*, and thus Novozym® 51032 is produced.

Specifically, in the present invention the above-mentioned Novozym® 51032 was used for hydrolysis of testosterone esters of formula (II) to testosterone (I).

The enzyme for the process of the invention can also be lipase from *Candida antarctica* A, also named lipase A from *Candida antarctica* or *Candida antarctica* lipase A or Ca/A, which is a well know enzyme, currently available on the market, for example, by Codexis Inc. (Redwood City, Calif. 94063, United States.)

Whichever is the enzyme used, the following embodiments describe various aspects of the invention.

According to a preferred embodiment of the invention, in the testosterone esters of formula (II) R is a $C_1$-$C_6$ linear or branched alkyl group, or is a $C_7$ branched cyclic alkyl group.

According to a preferred embodiment of the invention in the testosterone esters of formula (II) R is methyl, ethyl, 3-cyclopentylethyl, 2-methylbutanyl, n-hexyl or n-nonyl.

Testosterone ester of formula (II) wherein R is methyl has the following structure:

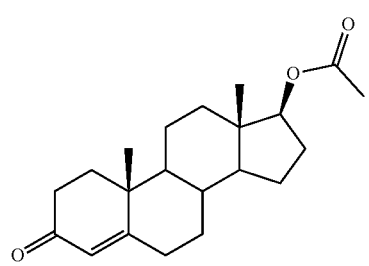 [SMILES: CC(=O)O[C@H]1CCC2C3CCC4=CC(=O)CC[C@]4(C)C3CC[C@@]21C]

and is also named as testosterone acetate.

Testosterone ester of formula (II) wherein R is ethyl has the following structure:

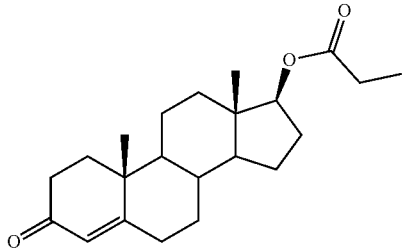 [SMILES: CCC(=O)O[C@H]1CCC2C3CCC4=CC(=O)CC[C@]4(C)C3CC[C@@]21C]

and is also named as testosterone propionate.

Testosterone ester of formula (II) wherein R is 3-cyclopentylethyl has the following structure:

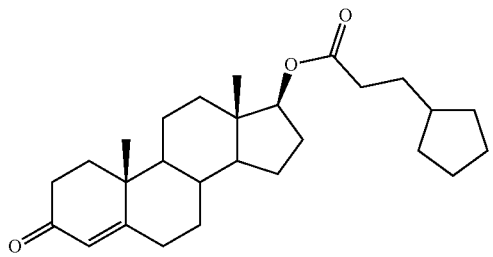 [SMILES: C[C@]12CCC(=O)C=C1CCC1C2CC[C@@]2(C)C1CC[C@@H]2OC(=O)CCC1CCCC1]

and is also named testosterone cypionate.

Testosterone ester of formula (II) wherein R is 2-methylbutanyl has the following structure:

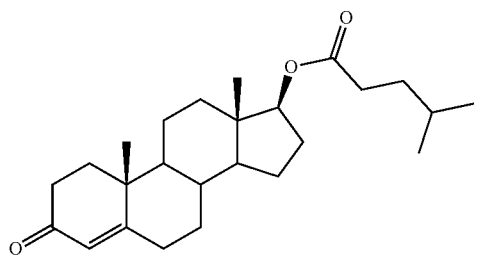 [SMILES: CC(C)CCC(=O)O[C@H]1CCC2C3CCC4=CC(=O)CC[C@]4(C)C3CC[C@@]21C]

and is also named testosterone isocaproate.

Testosterone ester of formula (II) wherein R is n-hexyl has the following structure:

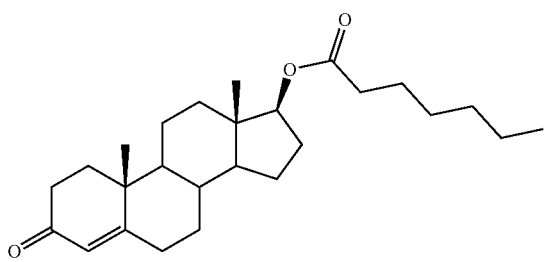 [SMILES: CCCCCCC(=O)O[C@H]1CCC2C3CCC4=CC(=O)CC[C@]4(C)C3CC[C@@]21C]

and is also named testosterone enantate.

Testosterone ester of formula (II) wherein R is n-nonyl has the following structure:

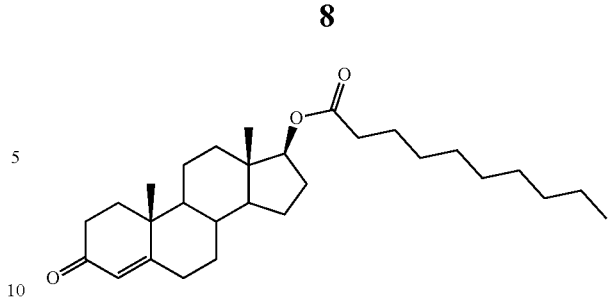

and is also named testosterone decanoate.

Testosterone esters of formula (II) wherein R is ethyl, 3-cyclopentylethyl, 2-methylbutanyl, n-hexyl or n-nonyl are substances pharmacologically active, currently on the market.

According to a more preferred embodiment of the invention, R is methyl or ethyl in the testosterone esters of formula (II) since they provide better conversions, with ethyl being the best since it provides the best conversions in the process of the invention.

According to a preferred embodiment of the invention, the amount of enzyme employed to perform the enzymatic hydrolysis of a testosterone ester of formula (II) is from 0.1 to 0.6 grams per gram of the compound of formula (II).

According to a preferred embodiment of the invention, the volume of buffer solution used is comprised between about 10 to about 40 volumes compared to the compound of formula (II).

Volume means volume of solvent per mass unit, i.e. 1 volume correspond e.g. to 1 ml per 1 g, or 1 liter per 1 Kg, or 1 microliter per 1 mg, etc.

The "buffer volumes" or "volume of buffer solution" means the amount, in terms of volumes, of buffer solution with reference to the amount of substrate used. Therefore, said definition is not an absolute measure, but a relative one as above described regarding to the meaning of volume or as exemplified in Example 5.

According to a preferred embodiment of the invention, the process is carried out at a temperature comprised between about 35° C. and about 70° C., more preferably at 65-70° C.

According to a preferred embodiment of the invention, the process is carried out at pH comprised between about 7.0 and about 10.0, more preferably between 7.0 and 7.5.

According to a preferred embodiment of the invention, the process is carried out according anyone of the following preferred conditions:
  the temperature is about 70° C. and pH is about 7.0, or
  the temperature is comprised between about 50° C. and about 70° C. and pH is comprised between about 7.0 and about 8.5, or
  the temperature is about 35° C. and pH is comprised between about 7.0 and about 10.0 and the amount of buffer solution is about 10 volumes.

According to a more preferred embodiment of the invention, the process is carried out according to the following preferred conditions:
  the temperature is about 70° C. and pH is about 7.0 and 10 volumes of buffer solution.

According to a preferred embodiment of the invention, in the testosterone esters of formula (II) R is ethyl.

According to a preferred embodiment of the invention, in the testosterone esters of formula (II) R is ethyl and the enzyme is Novozym® 51032. Novozym® 51032 is the cutinase which has been already above described.

According to an embodiment of the invention, the process can be carried out according to the following method comprising the following steps:
a) preparing an amount of hydrolytic enzyme,
b) adding an amount of substrate testosterone ester of formula (II),
c) diluting the preparation with buffer,
d) stirring the suspension,
e) obtaining the conversion of the compound of formula (II) to testosterone of formula (I).

According to an alternative embodiment of the invention, the process can be carried out according to the method above described wherein the step a) and the step b) can be reverted.

According to a preferred embodiment of the invention, the preparation of testosterone ester of formula (II):

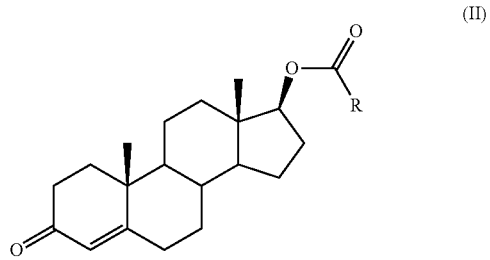

wherein R is a $C_1$-$C_9$ linear or branched alkyl group or is $C_3$-$C_9$ cyclic or branched cyclic alkyl group, is carried out by esterification of testosterone of formula (I):

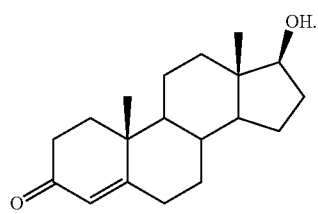

The esterification of testosterone (I) to provide testosterone esters (II) can be carried out according to the standard procedures known by the skilled person in organic synthesis which typically include, for example, the direct reaction of an acyl halide or with an acyl anhydride, preferably in presence of a base.

According a preferred embodiment, the esterification of testosterone to provide testosterone esters can be carried out by means of propionic anhydride or propionic chloride.

According a preferred embodiment, the esterification of testosterone to provide testosterone esters can be carried out in presence of a base, preferably DMAP (dimethylamminopyridine), pyridine, triethylamine, etc. . . .

According a preferred embodiment, the esterification of testosterone to provide testosterone esters can be carried out by means of propionic anhydride and DMAP.

In such a case, i.e. when the process also comprises this further previous reaction for the preparation of the starting material testosterone ester of formula (II) from testosterone (I), the whole process can be seen as a procedure to purify testosterone passing through the preparation and purification of testosterone esters of formula (II).

Another aspect of the present invention is the use of a lipase for the enzymatic hydrolysis of compound of formula (II):

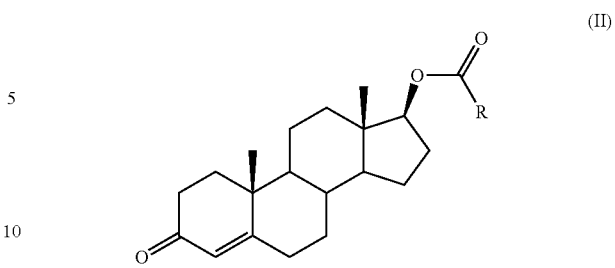

wherein R is a $C_1$-$C_9$ linear or branched alkyl group or is $C_3$-$C_9$ cyclic or branched cyclic alkyl group, to provide testosterone of formula (I):

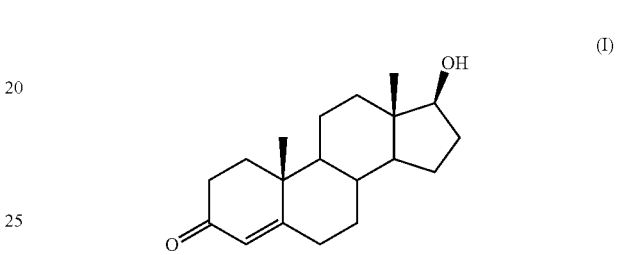

wherein the lipase is a lipase from *Aspergillus oryzae* or is a lipase from *Candida antarctica* A.

The lipase from *Aspergillus oryzae* is a lipase from *Humicola insolens*, wherein the DNA sequence encoding the *Humicola insolens* lipase is genetically modified or not genetically modified. Specifically said lipase from *Humicola insolens* can be also produced by a host cell, preferably in *Aspergillus oryzae*.

According to a more preferred embodiment of the invention, the use of a lipase from *Aspergillus oryzae* which is Novozym® 51032 is preferred.

Furthermore is preferred the use of Novozym® 51032, a lipase from *Humicola insolens*, wherein the DNA sequence encoding the *Humicola insolens* lipase is genetically modified. Said Novozym® 51032 is produced in the host cell, in particular by *Aspergillus oryzae*.

Novozym® 51032 of the present invention, a lipase from *Humicola insolens*, in particular is a cutinase, as already described above.

According to a preferred embodiment of the invention, the use of a lipase for the enzymatic hydrolysis of compound of formula (II) is preferred wherein in the compound of formula (II) R is ethyl.

According to a preferred embodiment of the invention, the use of a lipase from *Aspergillus oryzae* or lipase from *Candida antarctica* A for the enzymatic hydrolysis of compound of formula (II) is preferred wherein in the compound of formula (II) R is ethyl.

According to a preferred embodiment of the invention, the use of a lipase from *Aspergillus oryzae* which is Novozym® 51032 for the enzymatic hydrolysis of compound of formula (II) is preferred wherein in the compound of formula (II) R is ethyl.

According to a more preferred embodiment of the invention, the use of a lipase from *Humicola insolens*, wherein the DNA sequence encoding the *Humicola insolens* lipase is genetically modified or not genetically modified, or lipase from *Candida antarctica* A for the enzymatic hydrolysis of compound of formula (II) is preferred wherein in the compound of formula (II) R is ethyl.

According to a more particularly preferred embodiment of the invention, the use of a lipase from *Humicola insolens* which is Novozym® 51032 for the enzymatic hydrolysis of compound of formula (II) is preferred wherein in the compound of formula (II) R is ethyl.

An another object of the invention is a process for the preparation of a testosterone ester of formula (III):

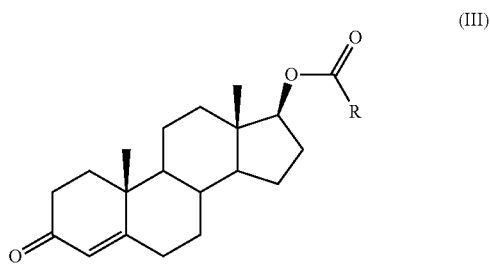

wherein R is a $C_1$-$C_9$ linear or branched alkyl group or is a $C_3$-$C_9$ cyclic or branched cyclic alkyl group,
comprising the following steps:
a) process for preparing testosterone of formula (I) according to the enzymatic process of the present invention, above described;
b) esterification reaction of testosterone of formula (I):

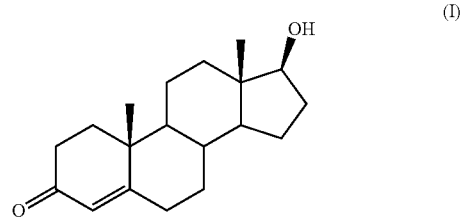 [SMILES: C[C@]12CCC(=O)C=C1CCC1C2CC[C@@]2(C)C1CC[C@@H]2O]

to provide testosterone ester of formula (III).

The meanings of R of the compound of formula (III) are the same of those given above for R of the compound of formula (II).

The conditions and preferred embodiments to carry out the step a) have been already above described.

Regarding to the conditions and preferred embodiments to carry out the step b), those have been already described above in the paragraphs describing the preparation of testosterone ester of formula (II):

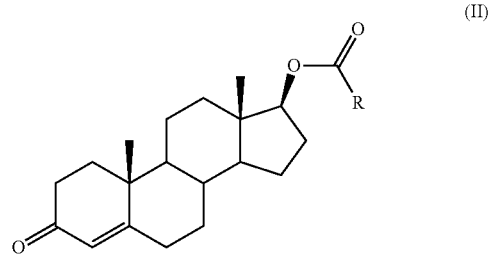

by esterification of testosterone of formula (I).

The process here described can be seen as a method for purifying the testosterone esters of formula (II) through the preparation of testosterone.

The process here described can be also seen as a method for preparing testosterone esters of formula (III) starting from different testosterone esters of formula (II), through the preparation of testosterone, as exemplified in the scheme below:

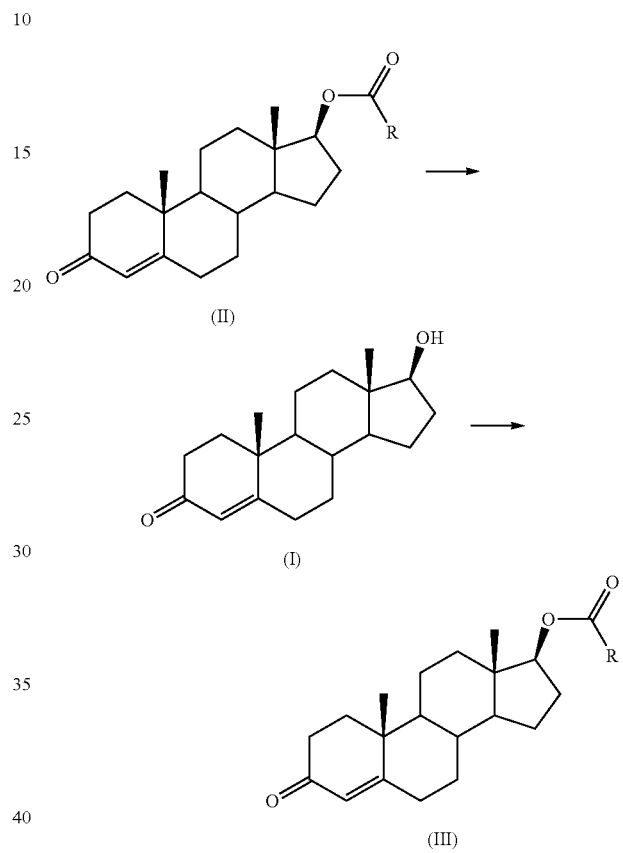

For example, according to the process of the invention, which includes the step of enzymatic hydrolysis, testosterone propionate can be converted to final product being testosterone cipionate or testosterone enantate or testosterone decanoate or testosterone isocaproate, through the preparation of testosterone above described.

According to a preferred embodiment of a process for the preparation of a testosterone ester of formula (III), in the testosterone ester of formula (III) R is ethyl, 3-cyclopentylethyl, 2-methylbutanyl, n-hexyl or n-nonyl.

According to a preferred embodiment of a process for the preparation of a testosterone ester of formula (III) in the starting material testosterone ester of formula (II) to carry out the step a) R is methyl or ethyl, preferably is ethyl.

According to a more preferred embodiment of a process for the preparation of a testosterone ester of formula (III), in the final product testosterone ester of formula (III) R is ethyl, 3-cyclopentylethyl, 2-methylbutanyl, n-hexyl or n-nonyl and in the starting material testosterone ester of formula (II) for carrying out the step a) R is ethyl.

An another object of the invention is a process for the preparation of a testosterone ester of formula (III):

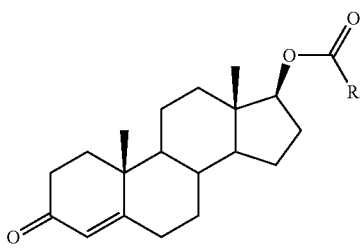

(III)

wherein R is a $C_1$-$C_9$ linear or branched alkyl group or is a $C_3$-$C_9$ cyclic or branched cyclic alkyl group, comprising the following steps:

a) preparation of testosterone ester of formula (II):

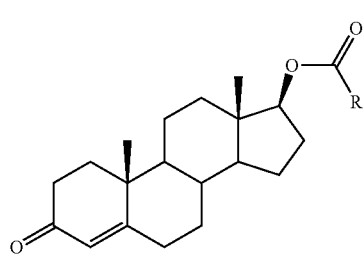

(II)

wherein R is a $C_1$-$C_9$ linear or branched alkyl group or is a $C_3$-$C_9$ cyclic or branched cyclic alkyl group, carried out by esterification of testosterone of formula (I):

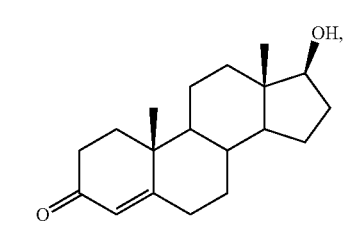

(I)

b) preparing testosterone of formula (I) according to the enzymatic process of the present invention, above described;
c) esterification reaction of testosterone of formula (I):

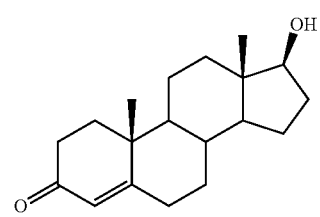

(I)

to provide testosterone ester of formula (III), wherein the meanings of R of the compound of formula (III) are the same of those given above for R of the compound of formula (II).

The conditions and preferred embodiments to carry out all the steps have been already above described.

The process here described can be also seen as a method for preparing testosterone esters of formula (III) starting from testosterone of formula (I), passing firstly through the preparation of testosterone esters of formula (II), then converting them to testosterone of formula (I) and finally converting it to testosterone esters of formula (III).

The scheme below shows this process of the invention:

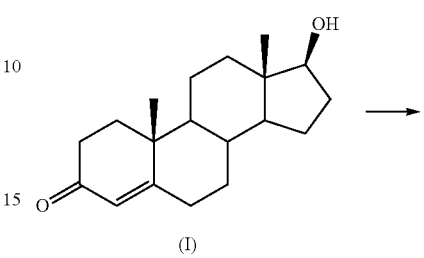

(I)

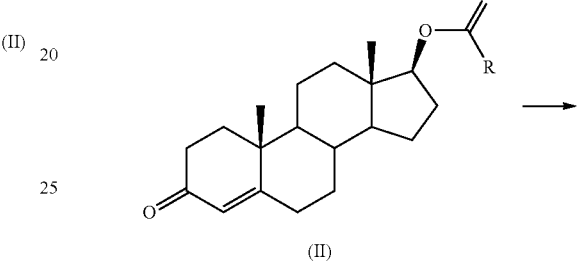

(II)

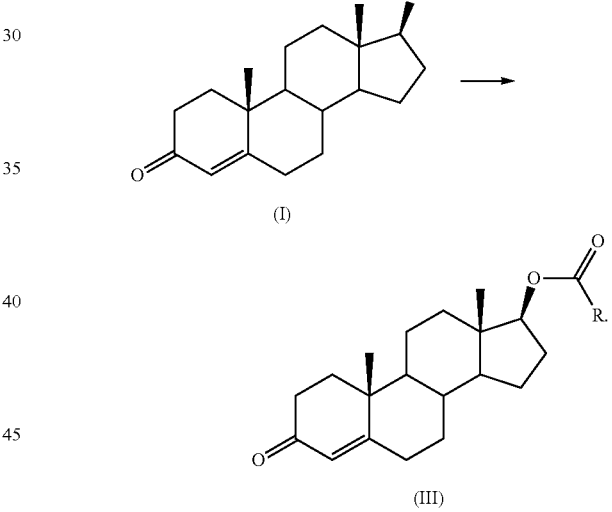

(I)

(III)

According to a preferred embodiment of the process for the preparation of a testosterone ester of formula (III), in the final product testosterone ester of formula (III) R is ethyl, 3-cyclopentylethyl, 2-methylbutanyl, n-hexyl or n-nonyl.

According to a preferred embodiment of the process for the preparation of a testosterone ester of formula (III), in the intermediate testosterone ester of formula (II) to carry out the step b) R is methyl or ethyl, more preferably is ethyl.

According to a more preferred embodiment of the process for the preparation of a testosterone ester of formula (III), in the final product testosterone ester of formula (III) R is ethyl, 3-cyclopentylethyl, 2-methylbutanyl, n-hexyl or n-nonyl and in the intermediate testosterone ester of formula (II) for carrying out the step b) R is ethyl.

The scheme below shows a preferred embodiment of this process of the invention:

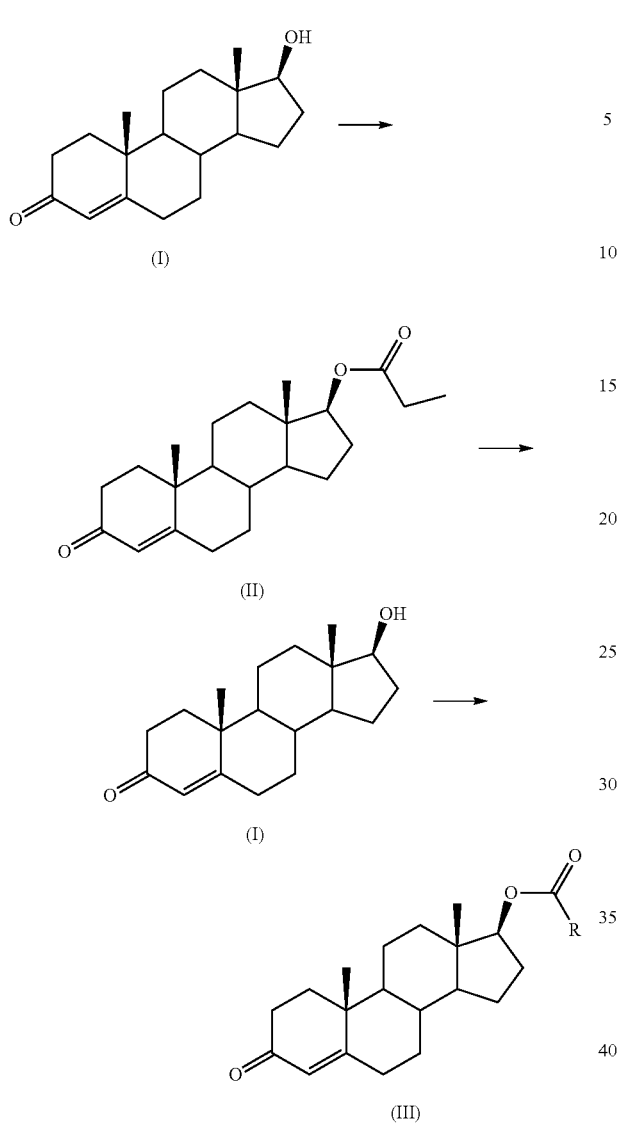

wherein in the compound of formula (III) R is ethyl, 3-cyclopentylethyl, 2-methylbutanyl, n-hexyl or n-nonyl.

As beforehand described, a further advantage of the process of the present invention is the process for the preparation of a testosterone ester of formula (III). Specifically, the latter process, which includes a specific step of the above-mentioned procedure, is carried out by the enzymatic hydrolysis of the invention, specifically by means of the use of the enzyme, which is a lipase from *Aspergillus oryzae* (*Humicola insolens* cutinase) or lipase from *Candida antarctica* A. Furthermore, the obtained testosterone ester of formula (III) has high chemical purity since the reaction is extremely regioselective, as earlier described.

The following experiments give evidence of the effect provided by the enzymes of the invention giving a strong improvement in terms of conversions of testosterone esters to testosterone.

Furthermore the effect given to the enzymatic hydrolysis by lipase from *Aspergillus oryzae*, specifically the lipase from *Aspergillus oryzae* which is Novozym® 51032, or lipase from *Candida antarctica* A, is highlighted in terms of higher chemical purity of testosterone obtained from testosterone ester since in this transformation are not generated impurities, being the enzyme extremely regioselective.

Experimental Section

The starting material testosterone is a substance commercially available. testosterone ester, in particular testosterone acetate and testosterone propionate can be produced by reacting testosterone respectively with acetic or propionic anhydride, testosterone enantate and testosterone cypionate can be produced by reacting testosterone with the related acyl acid.

Example 1: Synthesis of Testosterone of Formula (I) by Chemical Hydrolysis of Testosterone Esters of Formula (II)—Comparative Tests 100 mg testosterone acetate in 3 ml of methanol was hydrolyzed using 125 ul of NaOH solution (30%). Conversion was evaluated after 24 h of stirring with incubation at room temperature. Analogue reaction was performed using testosterone cypionate, testosterone enantate, testosterone propionate. The HPLC analysis carried out at the end of the reaction (below of 0.1% A/A % of reactant) show that the chemical purity of testosterone is comprised between 60 and 75% A/A %, the rest being several unknown impurities (>0.1%).

Example 2: Synthesis of Testosterone of Formula (I) by Enzymatic Hydrolysis of Testosterone Esters of Formula (II)—Reworking Prior Art Experiment (Tetrahedron Letters, 28 (52), 6549-6552, 1987, Entries 9 and 10 of Table of Page 6551)—Enzymatic Hydrolysis Performed with *Candida cylindracia* Lipase (*C. rugosa*)

A) 100 mg testosterone acetate in 3 ml of phosphate buffer 0.1 M pH 8 was tentatively hydrolyzed using Lipase from *Candida rugosa* (30 mg) (purchased from Sigma-Aldrich code 62316). Conversion was evaluated after 20 h of stirring with incubation at room temperature and conversion to testosterone (I) reached about 1.7%.

B) Analogue trial was performed where 100 mg testosterone propionate in 3 ml of phosphate buffer 0.1 M pH 8 was tentatively hydrolyzed using Lipase from *Candida rugosa* (30 mg) (purchased from Sigma-Aldrich code 62316). Conversion was evaluated after 20 h of stirring with incubation at room temperature and conversion to testosterone (I) reached about 9%.

These results confirms substantially the poor results achieved with the enzyme of the prior art.

Example 3: Synthesis of Testosterone of Formula (I) by Enzymatic Hydrolysis of Testosterone Esters of Formula (II)—According to the Invention with Lipase from *Candida antarctica* A (Ca/A)

A) 100 mg of testosterone enanthate in 3 ml of phosphate buffer 0.1 M pH 8 was hydrolyzed using Ca/A (30 mg) (purchased from Codexis Inc.). Conversion was evaluated after 20 h of stirring with incubation at room temperature and conversion reached about 88%.

B) 100 mg of testosterone propionate in 3 ml of phosphate buffer 0.1 M pH 8 was hydrolyzed using Ca/A (30 mg). Conversion was evaluated after 20 h of stirring with incubation at room temperature and conversion reached about 82%.

Example 4: Synthesis of Testosterone of Formula (I) by Enzymatic Hydrolysis of Testosterone Esters of Formula (II)—According to the Invention with a Lipase from *Aspergillus oryzae*, in Particular Novozym® 51032

Novozym® 51032 is a cutinase from *Humicola insolens*, wherein the DNA sequence encoding the *Humicola insolens* cutinase is genetically modified, and said cutinase is produced by *Aspergillus oryzae*.

A) 100 mg of testosterone enanthate in 3 ml of phosphate buffer 0.1 M pH 8 was hydrolyzed using Novozyme® 51032 (1 ml) (purchased form Novozymes). Conversion was evaluated after 20 h of stirring with incubation at room temperature and conversion reached about 64%.

B) 100 mg of testosterone cypionate in 3 ml of phosphate buffer 0.1 M pH 8 was hydrolyzed using Novozyme® 51032 (1 ml). Conversion was evaluated after 20 h of stirring with incubation at room temperature and conversion reached about 65%.

C) 100 mg of testosterone acetate in 3 ml of phosphate buffer 0.1 M pH 8 was hydrolyzed using Novozyme® 51032 (1 ml). Conversion was evaluate after 20 h of stirring with incubation at room temperature and conversion reach 99.13%. The HPLC purity of testosterone, in solution and at that stage of conversion, is 99.13% (HPLC A/A %), the rest being residual testosterone acetate (0.87%), only.

Example 5: Synthesis of Testosterone of Formula (I) by Enzymatic Hydrolysis of Testosterone Propionate of Formula (II)—According to the Invention with a Lipase from *Aspergillus oryzae*, in Particular Novozym® 51032

2500 mg of testosterone propionate in a phosphate buffer 0.1 M pH 8 solution was hydrolyzed using Novozyme® 51032 (2.5 ml). Conversion was evaluated after 6, 12, 24, 32 h of stirring under the conditions hereafter specified:
Temperature 35-70° C.
pH 7.0-10.0
dilution (i.e. volumes of buffer solution) 10-40 volumes
The following table resumes the results of the experimental trials:

| entry | pH | temp. ° C. | volumes | Conversion % 6 h | Conversion % 12 h | Conversion % 24 h | Conversion % 32 h |
|---|---|---|---|---|---|---|---|
| 1 | 10 | 35 | 10 | 25.50 | 49.70 | 81.00 | 97.50 |
| 2 | 8.5 | 52.5 | 25 | 62.23 | 97.03 | 99.50 | 99.49 |
| 3 | 7 | 70 | 10 | 99.00 | 99.00 | 99.23 | 99.37 |
| 4 | 10 | 35 | 40 | 14.81 | 28.53 | 55.70 | 76.91 |
| 5 | 7 | 35 | 40 | 12.6 | 25.00 | 48.59 | 70.20 |
| 6 | 7 | 35 | 10 | 26.60 | 55.00 | 94.76 | 99.20 |
| 7 | 8.5 | 52.5 | 25 | 55.00 | 91.50 | 99.05 | 99.45 |
| 8 | 7 | 70 | 40 | 91.83 | 99.06 | 99.29 | 99.40 |
| 9 | 8.5 | 52.5 | 25 | 60.74 | 95.39 | 99.28 | 99.41 |

The last columns of the table above clearly show the effect of the invention.

Example 6: Synthesis of Testosterone Propionate

A 1 Liter 4-RBF was charged with 150 g of Testosterone, 450 mL of Pyridine.

The suspension was stirred until complete dissolution, then were added 7.5 g of dicalite.

The reaction mixture was heated at 80° C. for 30 minutes, then the mixture was filtered on dicalite panel and the cake was washed 150 mL of pyridine. This washing was added to the previous filtered solution.

The whole filtered solution was transferred in a 2 Liter jacked reactor, then, at 25° C., are added 4.5 g of DMAP (4-dimethylaminopyridine).

In 45 minutes, 91 g of propionic anhydride were added by dropping.

After the end of the addition, the solution was stirred for 2 hours at 25° C. then 1200 mL of demineralized water were added over 60 minutes at 25° C. The solution was filtered on paper and the cake was washed with demineralized water at 35° C. The cake was discharged and dried in oven under vacuum at 70° C. 166.5 g of testosterone propionate were obtained.

The invention claimed is:

1. Process for the preparation of testosterone of formula (I):

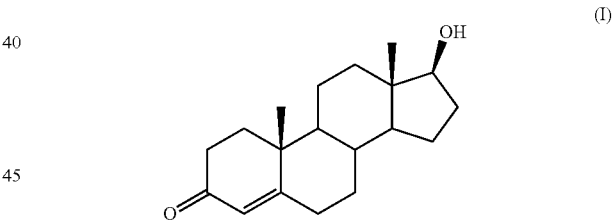

by performing an enzymatic hydrolysis of a testosterone ester of formula (II) in an aqueous buffer solution comprising an enzyme and the compound of formula (II):

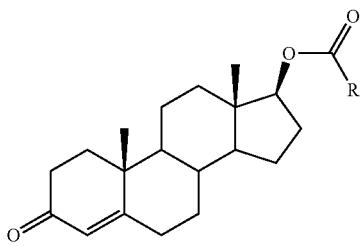

wherein R is a $C_1$-$C_9$ linear or branched alkyl group or is a $C_3$-$C_9$ cyclic or branched cyclic alkyl group, wherein the enzyme is a *Humicola insolens* lipase and DNA sequence encoding the *Humicola insolens* lipase is genetically modified or not genetically modified, or wherein the enzyme is *Candida antarctica* lipase A.

2. Process according to the claim 1, wherein said *Humicola insolens* lipase is a cutinase that has been recombinantly produced in *Aspergillus oryzae* as a host cell.

3. Process according to claim from 1, wherein in the testosterone esters of formula (II) R is a $C_1$-$C_6$ linear or branched alkyl group, or is a $C_7$ branched cyclic alkyl group.

4. Process according to claim 1, wherein R is methyl, ethyl, 3-cyclopentylethyl, 2-methylbutanyl, n-hexyl or n-nonyl.

5. Process according to claim 1, wherein volume of the buffer solution used is between about 10 to about 40 volumes in relation to the volume of the compound of formula (II).

6. Process according to claim from 1, wherein the process is carried out at a temperature between about 35° C. and about 70° C.

7. Process according to claim 1 wherein:
the temperature is about 70° C. and pH of the buffer solution is about 7.0, or
the temperature is between about 50° C. and about 70° C. and pH of the buffer solution is between about 7.0 and about 8.5, or
the temperature is about 35° C. and pH of the buffer solution is between about 7.0 and about 10.0, and the amount of the buffer solution is about 10 volumes in relation to the volume of the compound of formula (II).

8. Process according to claim 2, wherein in the testosterone esters of formula (II), R is ethyl.

9. Process according to claim 1, wherein the preparation of testosterone ester of formula (II):

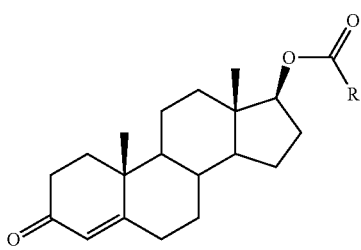

wherein R is a $C_1$-$C_9$ linear or branched alkyl group or is a $C_3$-$C_9$ cyclic or branched cyclic alkyl group, is carried out by esterification of testosterone of formula (I):

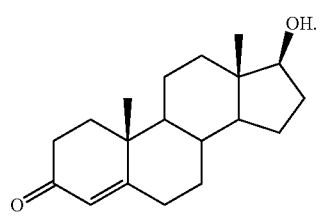

10. Process for the preparation of a testosterone ester of formula (III):

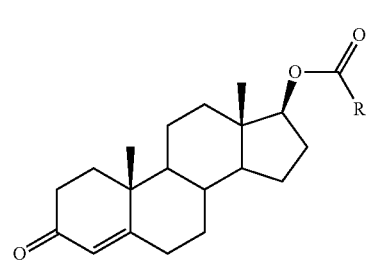

wherein R is a $C_1$-$C_9$ linear or branched alkyl group or is a $C_3$-$C_9$ cyclic or branched cyclic alkyl group, comprising the following steps:

a) preparing testosterone of formula (I) according to claim 1; and b) esterifying the testosterone of formula (I):

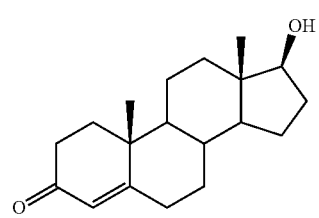

to provide testosterone ester of formula (III).

11. Process according to claim 10, wherein in the testosterone ester of formula (III), R is ethyl, 3-cyclopentylethyl, 2-methylbutanyl, n-hexyl or n-nonyl.

12. Process according to claim 11, wherein in the testosterone ester of formula (II) for carrying out the step a), R is ethyl.

* * * * *